United States Patent
Spahn

(10) Patent No.: US 7,463,715 B2
(45) Date of Patent: Dec. 9, 2008

(54) SYSTEM AND METHOD FOR REAL TIME DUAL ENERGY X-RAY IMAGE ACQUISITION

(75) Inventor: Martin Spahn, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1 day.

(21) Appl. No.: 11/846,800

(22) Filed: Aug. 29, 2007

(65) Prior Publication Data
US 2008/0198963 A1    Aug. 21, 2008

Related U.S. Application Data

(60) Provisional application No. 60/893,157, filed on Mar. 6, 2007, provisional application No. 60/890,662, filed on Feb. 20, 2007.

(51) Int. Cl.
*H05G 1/64*    (2006.01)
(52) U.S. Cl. ............... 378/98.12; 378/19; 378/98.9; 378/114
(58) Field of Classification Search ......... 378/4–20, 378/98.8, 98.9, 98.11, 98.12, 114–116; 382/131, 382/132
See application file for complete search history.

(56) References Cited

U.S. PATENT DOCUMENTS

2005/0113681 A1    5/2005    DeFreitas et al.
2005/0220265 A1    10/2005    Besson
2005/0226375 A1    10/2005    Eberhard et al.
2007/0114424 A1    5/2007    Danielsson
2007/0116179 A1    5/2007    Spahn et al.

OTHER PUBLICATIONS

Martin Spahn, Flat Detectors and Their Clinical Applications, Eur Radiol (2005) 15: 1934-1947 DOI 10.1007/s00330-005-2734-9 Received: Nov. 22, 2004, Revised: Feb. 8, 2005, Accepted: Mar. 1, 2005, Published Online: Apr. 2, 2005.
Henry C. Lukaski, Soft Tissue Composition and Bone Mineral Status: Evaluation by Dual-Energy X-Ray Absorptiometry, The Journal of Nutrition; United States Department of Agriculture, Agricultural Research Service, Grand Forks Human Nutrition Research Center, Grand Forks, ND 58202; 0022-3166/93 1993 American Institute of Nutrition.

*Primary Examiner*—Jurie Yun
(74) *Attorney, Agent, or Firm*—Alexander J. Burke; Peter L. Kendall

(57) ABSTRACT

An improved system and method for using dual energy techniques for acquiring x-ray images in two and three dimensions is disclosed. An X-ray source and detector are mounted at opposite ends of a movable C-arm. A fast movement mechanism is provided to quickly and precisely move the C-arm and detector in stepped motion about a patient. Low and high energy X-ray images are taken at each discrete step point, followed by fast movement of the source and detector to a next position with respect to the patient. Motion artifacts are eliminated by taking the high and low energy X-ray images while the C-arm is stopped. High and low energy pulses are provided through the use of a filtration arrangement which is synchronized with the frame rate of the detector to thereby optimize image collection.

20 Claims, 4 Drawing Sheets

SYSTEM AND METHOD FOR REAL TIME DUAL ENERGY X-RAY IMAGE ACQUISITION

CROSS REFERENCE TO RELATED APPLICATIONS

This is a non-provisional of pending U.S. provisional patent application Ser. No. 60/893,157, filed Mar. 6, 2007, by Martin Spahn, titled "Dual Energy Applications in Real Time," and is also a non-provisional of pending U.S. provisional patent application Ser. No. 60/890,662, filed Feb. 20, 2007, by Martin Spahn, titled "Dual Energy Applications in Real Time," the entirety of which applications are explicitly incorporated by reference herein.

FIELD

An embodiment of the invention is generally related to the field of dual energy techniques used in radiographic procedures, and more particularly to an improved system and method for using dual energy techniques for acquiring x-ray images in two and three dimensions that reduce motion artifacts and enable the building of highly refined 2D images and 3D volumes.

BACKGROUND

Dual energy x-ray techniques are known for use in medical imaging of tissue segments which consist of multiple components (e.g., bone, fat, soft tissue) that attenuate x-rays at different levels. When x-rays pass through such complex tissue segments, the beam is attenuated in proportion to the composition of the material, the thickness of the material and its individual components. The transmitted intensity depends on the intensity of the beam at its source, the energy attenuation coefficient and the density of the material. Dual energy refers to the use of two X-ray beams of differing spectral energy levels directed at a single targeted tissue region at different points in time. Each of the spectra provides an enhanced resolution of a certain type of tissue (e.g., bone, soft tissue, blood vessels, tumors). The two resultant images may then be superposed (i.e. combined) in a variety of ways such as by adding or subtracting portions or percentages of one or both images. These superposition variables can be selected by the user in order to highlight different tissues in a region of interest. For example, appropriate superposition of the two resultant images may allow the user to view either the high contrast structure (bones) or the low contrast structure (blood vessels and possible tumor). Digital imaging is often used to perform this procedure, for example using flat x-ray detectors and a digital image processing pipeline. The two different spectra needed to create the two images are often generated by changing the generator high voltage (kV) and/or the use of x-ray tube filtration.

Dual energy imaging has been used, for example, in thoratic imaging, in which two x-ray images (again, with two different x-ray spectra) are taken of the thorax within a short time period (sub-second). The short time period between acquisition of images is intended to reduce motion artifacts, which can reduce the clarity of the resulting superposed image. To enable use at a variety of patient positions, the x-ray source can be mounted on a C-arm so that it can be movable about the patient.

One problem with this arrangement is that conventional systems use a constant-movement C-arm, and thus, even though the pair of images (one low energy and one high energy) are taken successively within fractions of a second of each other, there still remains a slight difference between the portion of the tissue being imaged using the low and high energy x-rays. This is undesirable because the two images will, necessarily, be of slightly different sections of tissue, hindering the production of a high quality superposed image by introducing "motion artifacts" into the resulting image. Thus, there is a need for a high-speed system for obtaining dual energy images of selected tissue regions, which enables the fast production of a library of 2D images and 3D volumes of a targeted tissue area, and which eliminates motion artifacts common with current systems.

SUMMARY

A method for dual energy x-ray imaging is disclosed, comprising positioning an object between an x-ray source and an x-ray detector at a first position; imaging a first portion of the object by providing x-rays of a first energy from the source that pass through the object and impinge on the detector to create a first set of image data; imaging the first portion of the object by providing x-rays of a second energy from the source that pass through the object and impinge upon the detector to create a second set of image data, the second energy being different from the first energy; superposing the first and second sets of image data to generate a first superposed x-ray image; moving the x-ray source and detector to a second position with respect to the object; imaging a second portion of the object with x-rays of said first energy from the source that pass through the object and impinge on the detector, thus creating a third set of image data; imaging the second portion of the object with x-rays of said second energy from the source that pass through the object and impinge upon the detector, thus creating a fourth set of image data; and superposing the third and fourth sets of image data to generating a second superposed x-ray image wherein the steps of imaging the first and second portions of the object are synchronized with an acquisition frame rate of the x-ray detector.

A system for dual energy x-ray imaging is disclosed, comprising means for positioning an object between an x-ray source and an x-ray detector at a first position, means for imaging a first portion of the object by providing x-rays of a first energy from the source that pass through the object and impinge on the detector to create a first set of image data, means for imaging the first portion of the object by providing x-rays of a second energy from the source that pass through the object and impinge upon the detector to create a second set of image data, the second energy being different from the first energy, means for superposing the first and second sets of image data to generate a first superposed x-ray image, means for moving the x-ray source and detector to a second position with respect to the object, means for imaging a second portion of the object with x-rays of said first energy from the source that pass through the object and impinge on the detector, thus creating a third set of image data, means for imaging the second portion of the object with x-rays of said second energy from the source that pass through the object and impinge upon the detector, thus creating a fourth set of image data; and means for superposing the third and fourth sets of image data to generating a second superposed x-ray image, wherein the steps of imaging the first and second portions of the object are synchronized with an acquisition frame rate of the x-ray detector.

A machine readable storage device tangibly embodying a series of instructions executable by the machine to perform a series of steps is also disclosed. The steps may comprise positioning an object between an x-ray source and an x-ray detector at a first position; imaging a first portion of the object by providing x-rays of a first energy from the source that pass through the object and impinge on the detector to create a first set of image data; imaging the first portion of the object by providing x-rays of a second energy from the source that pass through the object and impinge on the detector to create a second set of image data, the second energy being different from the first energy; superposing the first and second sets of image data to generate a first superposed x-ray image; moving the x-ray source and detector to a second position with respect to the object; imaging a second portion of the object with x-rays of said first energy from the source that pass through the object and impinge on the detector, thus creating a third set of image data; imaging the second portion of the object with x-rays of said second energy from the source that pass through the object and impinge upon the detector, thus creating a fourth set of image data; and superposing the third and fourth sets of image data to generating a second superposed x-ray image; wherein the steps of imaging the first and second portions of the object are synchronized with an acquisition frame rate of the x-ray detector.

DETAILED DESCRIPTION

The present disclosure details a system and method for implementing high-speed dual energy x-ray imaging techniques to enable the building of high-resolution libraries of 2-dimensional images and/or 3-dimensional volumes. An exemplary embodiment makes dual energy applications more feasible for real time applications by synchronizing the change of the x-ray spectrum with the x-ray acquisition, and by providing high-speed synchronized stop-motion of the x-ray source and detector to eliminate motion artifacts common with current devices that use non-synchronized constant motion C-arms.

Figure 1:
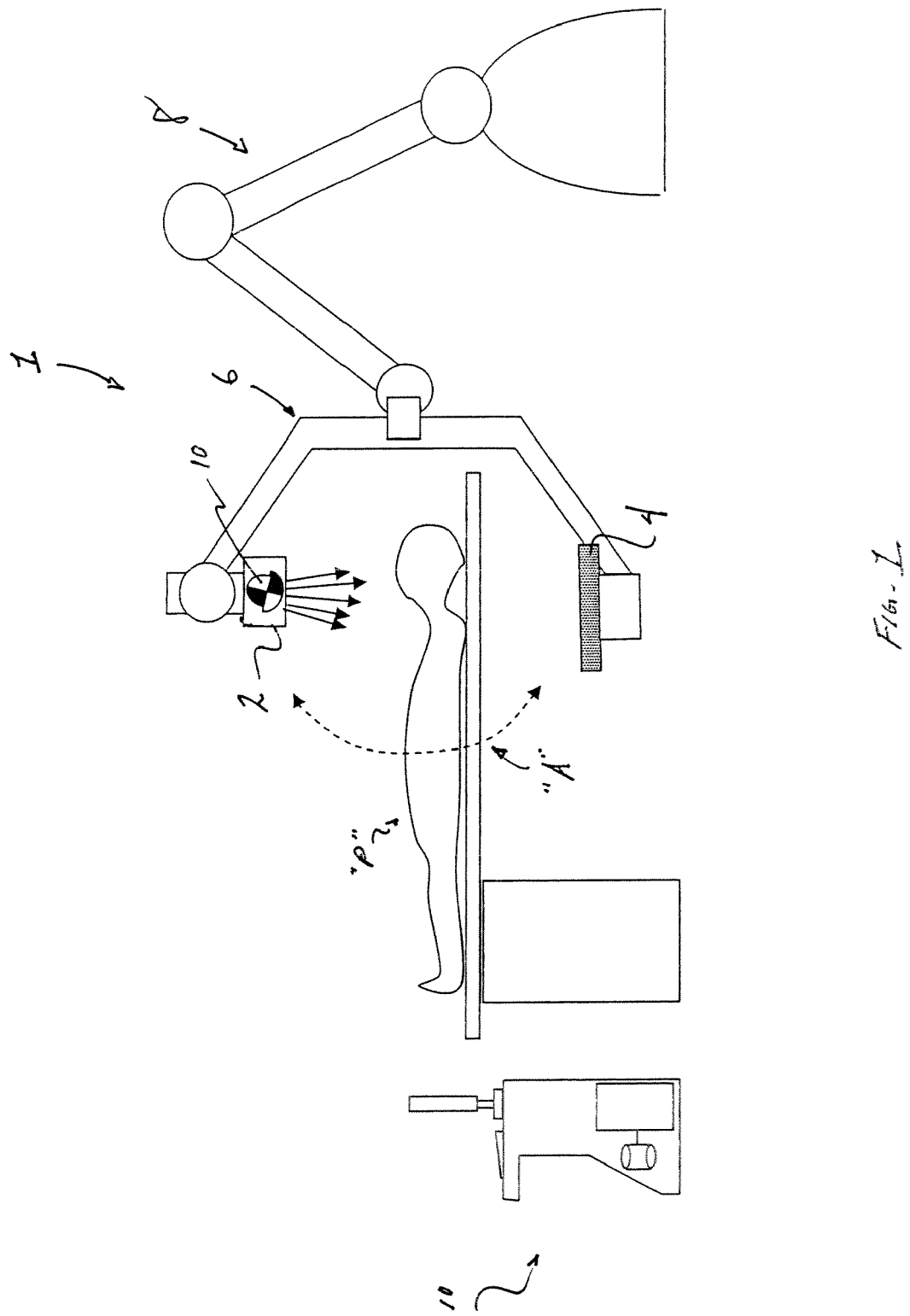
FIG. 1 is a diagram illustrating an isometric view of an imaging system according to the disclosure, including an x-ray source and detector held by a C-arm for movement about a patient.
Figure 2A:
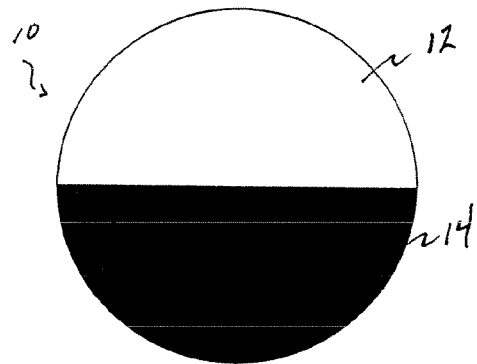
FIGS. 2A-2D are diagrams illustrating multiple embodiments of a rotating filter wheel (symmetric and asymmetric) for use with the system of FIG. 1.
Figure 2B:
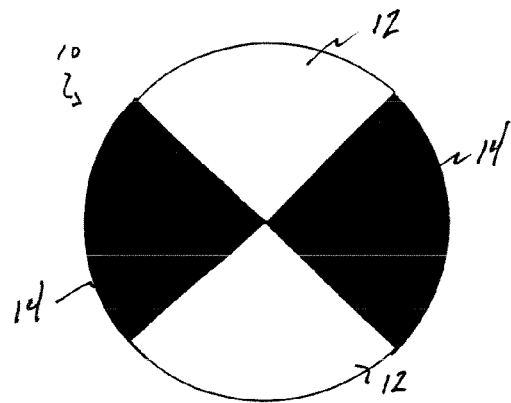
Figure 2C:
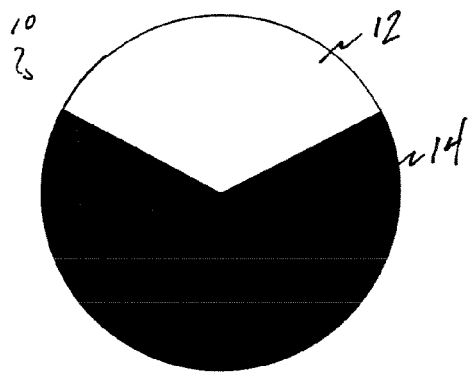
Figure 2D:
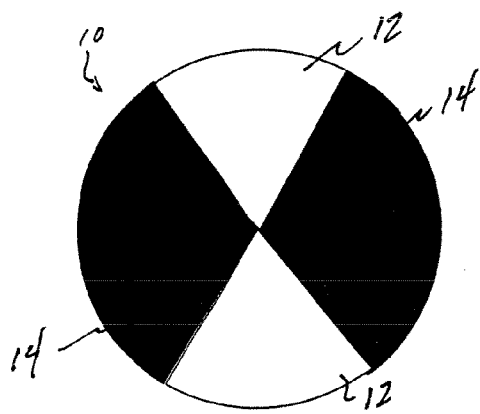

Referring to FIG. 1, a system 1 is illustrated comprising an x-ray source 2, a detector 4, and a C-arm 6 that fixes the source and detector 2, 4 at specific positions relative to each other. This C-arm 6 arrangement ensures that the patient "P" remains at the iso-center of source/detector 2, 4 pair. Such positioning ensures optimal and consistent detection of the X-rays over a variety of positionings. The C-arm 6 may be moved relative to the patient "P" by a movement mechanism 8, for example, allowing movement of the x-ray source 2 and detector 4 along the arc "A." The movement mechanism 8 may be controlled by computerized control system 10 that is either directly user controlled, or which is controlled by a processor running a series of pre-programmed instructions. The control system 10 may be employed to actuate the movement mechanism 8 (and the C-arm 6) in discrete, stepped movements relative to the patient "P." Thus the movement mechanism 8 may move the C-arm 6 to a specific position with respect to the patient, whereupon a pair of X-ray images are acquired (one at each energy level). Thereafter, the movement mechanism 8 may move the C-arm 6 to a next position with respect to the patient, a second pair of X-ray images are acquired (again, one at each energy level), and so on. This procedure may be repeated as many times as desired by the user in order to obtain a desired number of image "pairs," which may then be superposed to obtain a library of high resolution images. In one embodiment, the high resolution images may be assembled to obtain a 3D volume of a targeted area of interest.

As previously noted, prior devices used a voltage or current oscillation to effect a desired change in X-ray energy suitable for use in dual energy applications. In the present disclosure, the same "dual energy" effect is created by using a rotatable filter wheel 10 disposed between the X-ray source 2 and the patient "P". The filter wheel 8 may have alternating first and second regions 12, 14 of x-ray filtration materials. For example, the first region 12 may be substantially transparent to X-rays, thus enabling X-rays of a first predetermined energy level (low energy spectrum) to pass through and interact with patient tissue. The second region 14 may filter the X-rays emanating from the source 2 so that X-rays of a second predetermined energy level (high energy spectrum) pass through and interact with patient tissue. Thus, the filter wheel 10 may be rotated at a desired speed to produce sequences of "higher energy" and "lower energy" x-ray spectra, and hence a sequence of "high energy" and "low energy" images. In one embodiment, the filter wheel 10 is rotated at an angular rate which is synchronous with the frame rates of the detector 4 so that one image is taken with the filtration, the next without, the third with filtration, etc. In one embodiment, where the detector 4 is a flat panel detector, acquisition rates may be from about 30 to 60 frames per second.

In one exemplary embodiment, the first region 12 may be a transparent segment of the wheel 10, while the second region 14 may be a segment of the wheel containing a thin layer (e.g., 1 millimeter) of copper (Cu). Alternatively, the first region 12 may have light filtering (e.g., 0.5 mm Cu), while the second region 14 may have heavier filtering (e.g., 1.0 mm Cu). It will be appreciated that other filtration materials (aluminum, titanium) and thicknesses may also be used, as desired. Additionally, more than 2 filter regions could be used. For example, a first region could be transparent, a second region could have a 0.5 mm thickness of Cu, and a third region could comprise a 1.5 mm thickness of Cu.

In an alternative embodiment, a filter segment (0.5 mm Cu or 1.0 mm Cu, etc.) could be linearly moved in and out of the X-ray source path using a piezo or other small linear motor.

As can be seen in FIGS. 2A-2D, the filtration arrangement of the filter wheel 10 may be varied, depending upon the desired implementation. For example, the wheels 10 of FIGS. 2A and 2B may have first and second regions 12, 14 that are identically-sized and shaped so as to produce low and high energy X-ray pulses of the same duration (based on a given rotation rate of the filter wheel 10). By contrast, the wheels 10 shown in FIGS. 2C and 2D may have asymmetric first and second regions 12, 14. Thus, the first regions 12 may be are smaller than the second regions 14, which will provide a longer filtered X-ray pulse and a shorter unfiltered X-ray pulse.

Such an asymmetric arrangement of first and second regions 12, 14 may be important because the image taken with the filter (e.g., second region 14 with 1 mm thickness Cu) will generate a lower X-ray "dose" than the image taken without filter (e.g., first region 12 with 0 mm Cu) because the filter (1 mm Cu) strongly reduces the incoming x-ray flux (number of x-rays per area and time units) hitting the patient. Providing a longer pulse through the filtered region 14 may enhance the image acquired with the filtered X-rays. Where the detector 4 is a flat panel detector, such an increased pulse length should be synchronous with the integration phase of the detector 4. This is because integrating X-ray detectors (e.g., amorphous silicon based active matrix flat panel detectors, CCD-based or CMOS-based) typically run in a mode where the acquisition process or cycle is divided in three distinct steps: (1) integration, (2) readout, and (3) reset. These steps are repeated for each frame (e.g., 30 frames per second). During integration, the pixels—for example, photodiodes—acquire and accumulate the charge being generated by the incoming X-rays. This time window is called the "integration window." The X-ray pulse, generated by the X-ray tube, is synchronized with this X-ray window. During readout, no charge is collected, but the charge of each individual pixel is read out, one after the other, or in a parallel process, amplified and converted from an analog to a digital signal. During reset, the pixels are reset to be ready again for the next acquisition cycle.

Thus, the integration and readout scheme for the flat panel detector would have to support a "long integration window," image readout, "short integration window," image readout, etc. The size and shape of each of the first and second regions 12, 14 of the filter wheel 10 may be selected, along with the rotation rate for the filter wheel, to provide high and low energy X-ray pulses of specific desired duration. As previously noted, the shape and rotation rate can be selected to correspond with the frame rates of the detector 4 to enable efficient acquisition of images at each target location.

Figure 3:
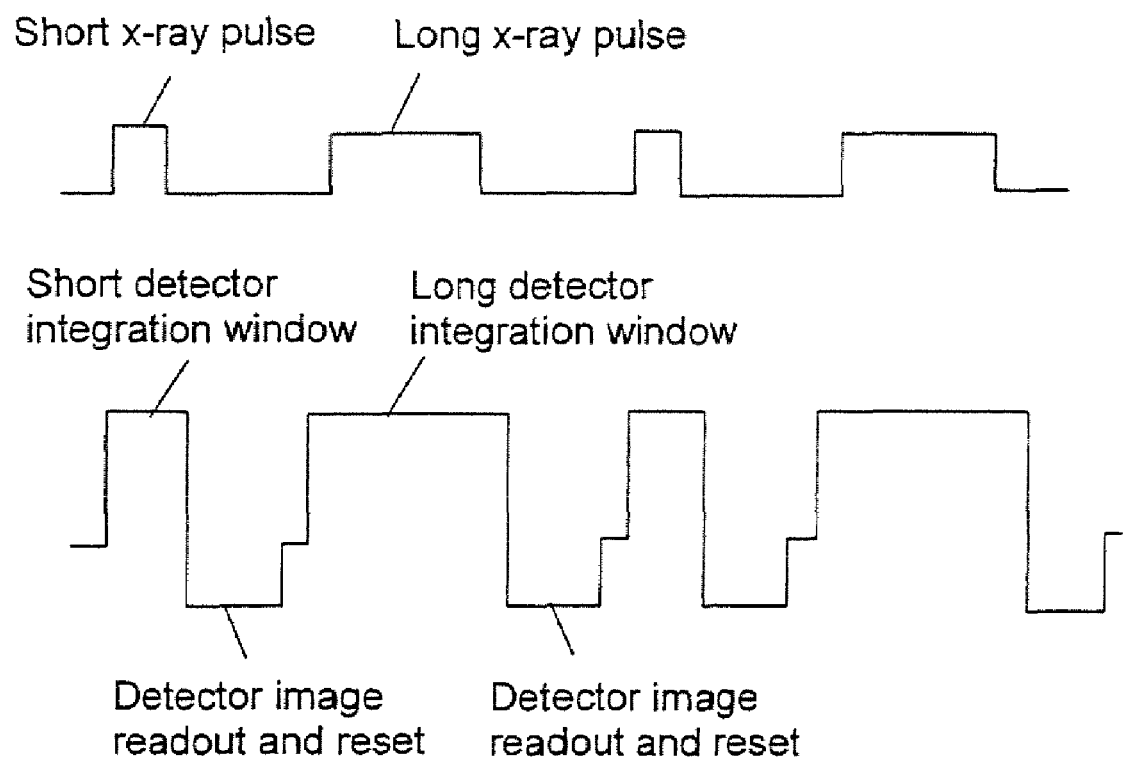
FIG. 3 is a diagram illustrating an asymmetric detector readout scheme for coping with sequences of longer and shorter x-ray pulse lengths.

Referring to FIG. 3, an asymmetric detector readout scheme is shown for coping with sequences of longer and shorter x-ray pulse lengths. As noted, the longer pulse length may be required to allow the generator to generate enough x-rays to adjust the dose level. The "high energy" spectrum is generated by filtering out more of the lower energy x-rays which has two effects: (i) providing a higher energy spectrum as desired, and (ii) fewer x-ray photons, i.e. less dose, which is not desired and which must be compensated for. The scheme of FIG. 3 shows the asymmetric implementation of the detector readout (long/short integration windows) to cope with long/short x-ray pulse lengths, possibly required due to the higher/lower x-ray filtration of the rotation wheel, as noted above.

In an alternative embodiment for compensating for the reduced dose inherent in the filtered X-ray pulse, the current supplied to the X-ray source may be increased by an appropriate amount during the period in which the pulse is being filtered.

As previously noted, a benefit of the disclosed system is that the filter wheel 10 can be rotated at a very fast rate (as fast as the frame rate of the detector 4). Thus, images with different x-ray spectra can be acquired in quasi-real time. Thus, every pair of images (i.e., one with filtration and one without filtration) are taken without noticeable change caused by system or patient movement. Hence each pair can be processed with superposition in order to generate an image with bony or low contrast content.

In one embodiment, rotation of the filter wheel 10 may coincide both with the acquisition rate of the detector 4 and the incremental stepping of the movement mechanism 8 and C-arm 6. The mechanical motion of the movement mechanism 8 and C-arm 6 may be synchronized by using fast robotics, thus enabling the disclosed acquisition technique to be applied to 3D imaging. Where the movement mechanism 8 is a high-speed robot, the robot can move the x-ray source 2, filter wheel 10 and detector 4 together immediately after a pair of images is acquired at a first location. A subsequent pair of images may then be acquired at a second location, followed by high-speed movement to a third location, and so on. Thus, through high-speed incremental movement of the robot a series of images can be acquired in quasi-real time (e.g. the robot 8 could move the X-ray source 2 and detector 4 to a next angular position after every pair of images is taken (such as by 1 degree), enabling the assemblage of a very large number of images into a 3-dimensional "volume." This is a distinct advantage over current systems which employ continuous frame rates (i.e., constant smooth motion of a C-arm), while maintaining a very high overall acquisition speed (quasi-real time).

Figure 4:
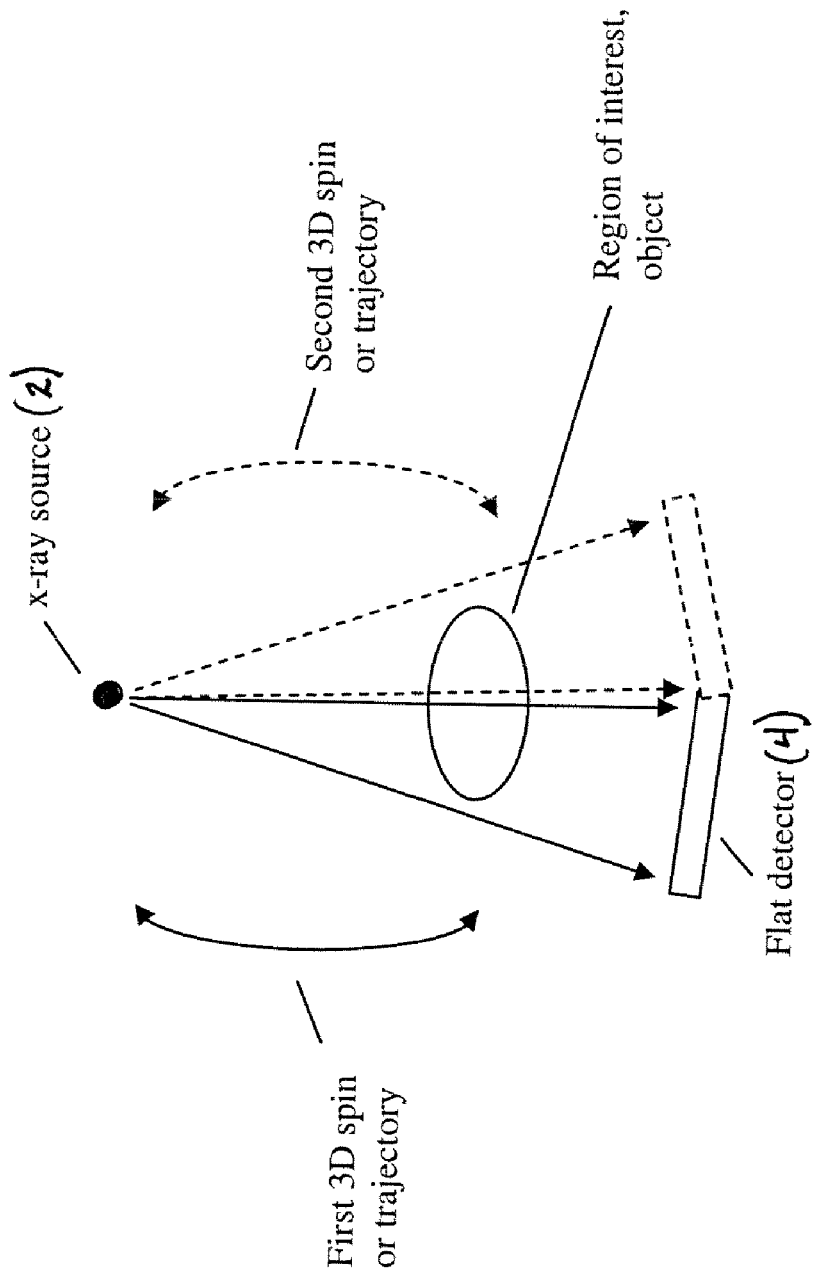
FIG. 4 is a diagram illustrating an exemplary manner in which the robot of FIG. 1 can change the positions and orientations of the detector and x-ray tube for enhanced.

The freely movable robotic arm of the movement mechanism 8 allows different trajectories around the object of interest than a pure translational movement or a rotational movement (of x-ray source and detector). As shown in FIG. 4, the movement mechanism 8 may enable first and second 3D spin or trajectory adjustments between the X-ray source 2 and detector 4. Such free trajectories are expected to make better use of the limited detector size and given object size in order to minimize truncation artifacts. (Truncation artifacts are image artifacts which result from insufficient information acquired about the object during the 3D run, and can occur if certain parts of the object are irradiated only during a portion of the projections during the 3D spin. The missing information generates artifacts during image reconstruction.) Additionally, a robotic arm 8 may allow movement of the x-ray source 2 and detector 4 around the targeted object several times using different trajectories and hence enlarging the region of interest. In one exemplary embodiment, the user can simulate twice the original detector size (at least in one the dimension perpendicular to the trajectory), thus enlarging the region of interest.

In a further embodiment, a C-arm 6 such as a DynaCT, manufactured by Siemens Medical Solutions, may be employed to operate at 30 frames per second in 1 degree incremental steps to provide the data to generate dual energy superposed 3D images. The C-arm may rotate around the patient table. The robotic arm 8, to which the C-arm is mounted, is used to move and control the proper projections needed to generate the desired data sets. With the DynaCT, where a large-size detector (e.g., 30 cm wide) is used, the patient table is stationary, and the patient volume (e.g., head or heart) can be acquired with one spin of slightly more than 180 degrees.

To provide even greater flexibility in providing X-rays of desired energies, the system 1 could employ a variable X-ray source (e.g., one whose voltage could be switched between high and low to provide corresponding high and low energy X-rays) in combination with a segmented rotating filter wheel 10.

Additionally, as will be appreciated, the highest frame rates of the detector 4 (30-60 frames per second (FPS) enable very fast movement around the patient, and are facilitated by use of the aforementioned asymmetric integration rates (FIG. 3). A fast 3D run performed in this way minimizes the impact of patient motion which can generate image artifacts. It will be appreciated that these numbers are merely exemplary, as future detectors may not be limited to 60 FPS, and are expected to perform at rates up to 100 FPS or more.

In a further alternative embodiment, a system may be implemented in which variable x-ray pulse lengths are triggered by the amount of radiation detected by the detector 4. Detectors with built in dose measuring devices or counting detectors may be used for such purposes. In this way, not only would the x-ray pulse lengths vary for the low and the high energy spectra but depending on the thickness of the object that needs to be penetrated at a given angulation the procedure could vary as the dose delivery depends highly on the thickness and material of the object.

The system described herein may be automated by, for example, tangibly embodying a program of instructions upon a computer readable storage media, capable of being read by machine capable of executing the instructions. A general purpose computer is one example of such a machine. Examples of appropriate storage media are well known in the art and would include such devices as a readable or writeable CD, flash memory chips (e.g., thumb drive), various magnetic storage media, and the like.

Various embodiments have been disclosed, and further variations will be apparent to persons skilled in the art. All such variations are considered to be within the scope of the appended claims. Reference should be made to the appended claims, rather than the foregoing specification, as indicating the true scope of the subject disclosure.

The invention claimed is:

1. A method for dual energy x-ray imaging, comprising:
    positioning an object between an x-ray source and an x-ray detector at a first position;
    imaging a first portion of the object by providing x-rays of a first energy from the source that pass through the object and impinge on the detector to create a first set of image data;
    imaging the first portion of the object by providing x-rays of a second energy from the source that pass through the object and impinge upon the detector to create a second set of image data, the second energy being different from the first energy;
    superposing the first and second sets of image data to generate a first superposed x-ray image;
    moving the x-ray source and detector to a second position with respect to the object;
    imaging a second portion of the object with x-rays of said first energy from the source that pass through the object and impinge on the detector, thus creating a third set of image data;
    imaging the second portion of the object with x-rays of said second energy from the source that pass through the object and impinge upon the detector, thus creating a fourth set of image data; and
    superposing the third and fourth sets of image data to generating a second superposed x-ray image;
    wherein the steps of imaging the first and second portions of the object are synchronized with an acquisition frame rate of the x-ray detector.

2. The method of claim 1, wherein the x-ray source and x-ray detector are connected by a C-arm, and the step of moving the x-ray source and detector is accomplished by moving the C-arm with respect to the object so that the object remains in the iso-center of the source and detector.

3. The method of claim 2, wherein the C-arm is connected to a high-speed movement mechanism, and the step of moving the x-ray source and detector is controlled step-wise along a predetermined path by an automated controller.

4. The method of claim 3, wherein the steps of providing x-rays of said first energy and providing x-rays of said second energy comprise providing a rotating filter wheel between said x-ray source and said object, wherein said filter wheel comprises at least one filtering region for changing an energy of x-rays that pass therethrough.

5. The method of claim 4, wherein said filter wheel further comprises at least one transparent region that is substantially transparent to x-rays, and wherein the filtering region takes up a substantially larger area of the filter wheel than the transparent region, the method further comprising rotating the filter wheel in synchronization with the acquisition frame rate of the x-ray detector.

6. The method of claim 5, further comprising repeating the imaging and moving steps to accumulate a library of image data sufficient to form a 3-dimensional image volume of at least a portion of said object.

7. A system for dual energy x-ray imaging, comprising:
    means for positioning an object between an x-ray source and an x-ray detector at a first position;
    means for imaging a first portion of the object by providing x-rays of a first energy from the source that pass through the object and impinge on the detector to create a first set of image data;
    means for imaging the first portion of the object by providing x-rays of a second energy from the source that pass through the object and impinge upon the detector to create a second set of image data, the second energy being different from the first energy;
    means for superposing the first and second sets of image data to generate a first superposed x-ray image;
    means for moving the x-ray source and detector to a second position with respect to the object;
    means for imaging a second portion of the object with x-rays of said first energy from the source that pass through the object and impinge on the detector, thus creating a third set of image data;
    means for imaging the second portion of the object with x-rays of said second energy from the source that pass through the object and impinge upon the detector, thus creating a fourth set of image data; and
    means for superposing the third and fourth sets of image data to generating a second superposed x-ray image;
    and means for synchronizing the steps of imaging the first and second portions of the object with an acquisition frame rate of the x-ray detector.

8. The system of claim 7, wherein the x-ray source and x-ray detector are connected by a C-arm, and the means for moving the x-ray source and detector comprises a C-arm that is movable with respect to the object so that the object remains in the iso-center of the source and detector.

9. The system of claim 8, wherein the C-arm is connected to a high-speed movement mechanism, and the means for moving the x-ray source and detector is controlled step-wise along a predetermined path by an automated controller.

10. The method of claim 9, wherein providing x-rays of said first energy and providing x-rays of said second energy comprise providing a rotating filter wheel between said x-ray source and said object, wherein said filter wheel comprises at least one filtering region for changing an energy of x-rays that pass therethrough.

11. The system of claim 10, wherein said filter wheel further comprises at least one transparent region that is substantially transparent to x-rays, and wherein the filtering region takes up a substantially larger area of the filter wheel than the transparent region, the system further comprising means for rotating the filter wheel in synchronization with the acquisition frame rate of the x-ray detector.

12. The system of claim 11, further comprising means for repeating the imaging and moving steps to accumulate a library of image data sufficient to form a 3-dimensional image volume of at least a portion of said object.

13. The system of claim 7, wherein the detector comprises a flat panel detector having an acquisition rate of from about 30 to about 60 frames per second.

14. A machine readable storage device tangibly embodying a series of instructions executable by the machine to perform a series of steps, the steps comprising:
    positioning an object between an x-ray source and an x-ray detector at a first position;
    imaging a first portion of the object by providing x-rays of a first energy from the source that pass through the object and impinge on the detector to create a first set of image data;
    imaging the first portion of the object by providing x-rays of a second energy from the source that pass through the object and impinge upon the detector to create a second set of image data, the second energy being different from the first energy;
    superposing the first and second sets of image data to generate a first superposed x-ray image;
    moving the x-ray source and detector to a second position with respect to the object;
    imaging a second portion of the object with x-rays of said first energy from the source that pass through the object and impinge on the detector, thus creating a third set of image data;
    imaging the second portion of the object with x-rays of said second energy from the source that pass through the object and impinge upon the detector, thus creating a fourth set of image data; and
    superposing the third and fourth sets of image data to generating a second superposed x-ray image;
    wherein the steps of imaging the first and second portions of the object are synchronized with an acquisition frame rate of the x-ray detector.

15. The machine readable storage device of claim 14, wherein the x-ray source and x-ray detector are connected by a C-arm, and the step of moving the x-ray source and detector is accomplished by moving the C-arm with respect to the object so that the object remains in the iso-center of the source and detector.

16. The machine readable storage device of claim 15, wherein the C-arm is connected to a high-speed movement mechanism, and the step of moving the x-ray source and detector is controlled step-wise along a predetermined path by an automated controller.

17. The machine readable storage device of claim 16, wherein the steps of providing x-rays of said first energy and providing x-rays of said second energy comprise providing a rotating filter wheel between said x-ray source and said object, wherein said filter wheel comprises at least one filtering region for changing an energy of x-rays that pass therethrough.

18. The machine readable storage device of claim 17, wherein said filter wheel further comprises at least one transparent region that is substantially transparent to x-rays, and wherein the filtering region takes up a substantially larger area of the filter wheel than the transparent region, the method further comprising rotating the filter wheel in synchronization with the acquisition frame rate of the x-ray detector.

19. The machine readable storage device of claim 18, further comprising repeating the imaging and moving steps to accumulate a library of image data sufficient to form a 3-dimensional image volume of at least a portion of said object.

20. The machine readable storage device of claim 14, wherein the detector comprises a flat panel detector having an acquisition rate of from about 30 to about 60 frames per second.

* * * * *